United States Patent [19]

Bartholomew et al.

[11] Patent Number: 5,176,662
[45] Date of Patent: Jan. 5, 1993

[54] SUBCUTANEOUS INJECTION SET WITH IMPROVED CANNULA MOUNTING ARRANGEMENT

[75] Inventors: Gerald Bartholomew, Sherman Oaks; Douglas G. Ritchie, Pasadena, both of Calif.

[73] Assignee: Minimed Technologies, Ltd., Sylmar, Calif.

[21] Appl. No.: 572,924

[22] Filed: Aug. 23, 1990

[51] Int. Cl.⁵ .............................................. A61M 5/00
[52] U.S. Cl. .................... 604/283; 604/164; 604/180; 604/167; 128/DIG. 26
[58] Field of Search ............... 604/93, 158, 164, 165, 604/167, 174, 175, 180, 240–243, 264, 272, 283, 905

[56] References Cited

U.S. PATENT DOCUMENTS

| | | | |
|---|---|---|---|
| 3,469,579 | 9/1969 | Hubert | 604/283 |
| 3,720,210 | 3/1973 | Diettrich | 604/283 |
| 4,037,599 | 7/1977 | Raulerson | 604/164 |
| 4,354,495 | 10/1982 | Bodicky | 604/283 |
| 4,409,046 | 10/1983 | Holzwarth et al. | 604/272 |
| 4,523,968 | 6/1985 | McCool | 604/283 |
| 4,755,173 | 7/1988 | Konopka et al. | 604/180 |
| 4,755,649 | 7/1988 | Barker et al. | 604/283 |
| 4,846,174 | 7/1989 | Willard et al. | 604/96 |
| 4,932,114 | 6/1990 | Morse et al. | 604/905 |

Primary Examiner—Stephen C. Pellegrino
Assistant Examiner—Ralph A. Lewis
Attorney, Agent, or Firm—Stuart O. Lowry; Leslie S. Miller

[57] ABSTRACT

An improved subcutaneous injection set is disclosed which has a soft cannula for subcataneous delivery of a selected medication to a patient. The cannula is supported by and protrudes outwardly from a cylindrical support hub of a housing adapted to receive the selected medication. A flanged base end of the cannula is disposed within the housing and is captured by a swaged lock rim to retain a sealing gasket under compression against an annular seat within the support hub, thereby preventing leakage of the medication through the hub and about the exterior of the cannula.

12 Claims, 2 Drawing Sheets

1

SUBCUTANEOUS INJECTION SET WITH IMPROVED CANNULA MOUNTING ARRANGEMENT

BACKGROUND OF THE INVENTION

Field of the Invention

This invention relates generally to injection devices for use with an external infusion system for subcutaneous delivery of a selected medication or other therapeutic fluid to a patient, and more particularly to an improved subcutaneous injection set of the type having a soft or flexible cannula, and further including improved sealing means for preventing undesired fluid leakage.

Subcutaneous injection sets are generally known in the art for use in delivering a selected medication or other therapeutic fluid to a desired subcutaneous site located beneath the skin of a patient. Such injection sets commonly include a relatively short cannula or catheter which is supported by and protrudes from a compact housing adapted to receive the infusion fluid via a delivery tube connected suitably to other components of a fluid infusion system.

An insertion needle is normally provided to extend through a lumen formed in the cannula to facilitate transcutaneous placement of the cannula, after which the insertion needle is withdrawn to leave the cannula in place for subcutaneous fluid infusion into the patient. A preferred subcutaneous injection set of this general type is described and claimed in commonly assigned U.S. Pat. No. 4,755,173, which is hereby incorporated herein by reference.

In prior subcutaneous injection sets, the selected infusion fluid is normally supplied to the patient under positive pressure flow conditions. As a result, manufacturing precautions have been required to prevent undesired leakage of the infusion fluid about the exterior of the cannula, and corresponding nondelivery of the infusion fluid to the patient. In the past, attempts to prevent such fluid leakage have included the use of adhesive agents and/or ultrasonic welding or other heat seal techniques intended to sealably fix the cannula to the injection set housing However, such sealing techniques have not provided the desired consistent level of leak-free reliability, possibly due to the use of incompatible materials to form the housing and cannula of the injection set.

There exists, therefore, a significant need for further improvements in subcutaneous injection sets, particularly with respect to providing an improved and reliably sealed mounting arrangement for a soft cannula with respect to an injection set housing. The present invention fulfills these needs and provides further related advantages.

SUMMARY OF THE INVENTION

In accordance with the invention, a subcutaneous injection set includes improved apparatus and a method for mounting a hollow cannula onto a relatively compact housing adapted to receive a selected medication or other therapeutic infusion fluid. The cannula, which preferably comprises a soft or flexible cannula, includes a flanged base end in cooperation with a resilient sealing gasket to positively prevent undesired fluid leakage about the cannula exterior.

In the preferred form of the invention, the subcutaneous injection set is constructed generally in accordance with U.S. Pat. No. 4,755,173, which is incorporated by reference herein. More specifically, the compact housing defines a chamber for receiving a selected medication or other infusion fluid via a delivery tube or the like. The infusion fluid passes from the housing chamber through a lumen defined by the cannula, wherein the cannula is supported by the housing to protrude outwardly from a generally cylindrical support hub. An insertion needle is initially received through the cannular lumen to facilitate transcutaneous cannula placement, after which the insertion needle is withdrawn from the injection set, leaving the cannula in place and permitting fluid flow through the cannular lumen to the subcutaneous injection site.

The base end of the cannula is disposed within the housing chamber and defines a radially enlarged flange which obstructs cannula removal from the housing through the support hub. An elastomeric sealing gasket such as a resilient O-ring is carried about the cannula in a position interposed axially between the flange and an annular seat at the upstream end of the support hub. An overlying lock rim is formed within the housing chamber to retain the cannular flange in bearing engagement against the sealing gasket, thereby preventing undesired fluid leakage through the support hub at the exterior of the cannula.

The lock rim is formed quickly and easily by inserting a swage tool into the housing chamber and deforming a portion of the housing while advancing the swage tool in a direction toward the flanged base end of the cannula. The preferred swage tool comprises a sonic horn having a beveled leading edge for sonically deforming plastic housing material to form the lock rim. Importantly, the position of the lock rim is designed to capture and maintain the flange in compressive engagement with the sealing gasket, to prevent undesired fluid leakage about the exterior of the cannula.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which.

DETAILED DESCRIPTION OF THE PREFERRED EMBODIMENT

Figure 1:
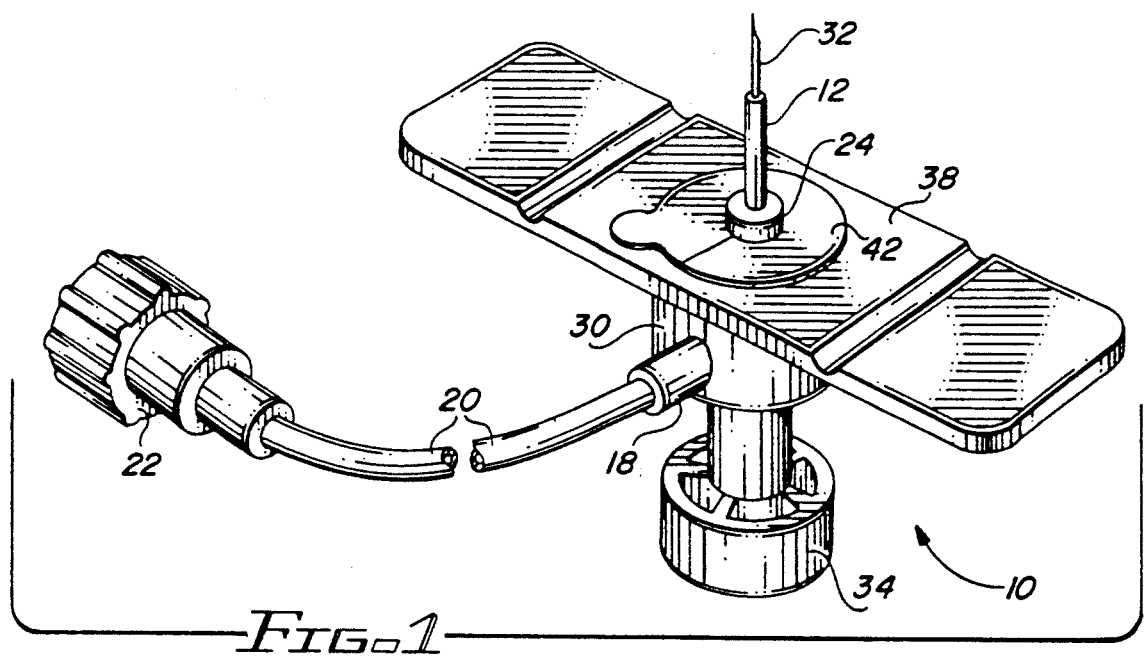
FIG. 1 is a perspective view of a subcutaneous injection set embodying the novel features of the invention.

As shown in the exemplary drawings, an improved subcutaneous injection set referred to generally in FIG. 1 by the reference numeral 10 is provided for subcutaneous delivery of a selected medication or other therapeutic infusion fluid to a patient. The improved injection set 10 includes a soft or flexible cannula 12 supported by a compact housing 14 to which the medication is supplied. In accordance with the invention, the cannula 12 is mounted to the housing 14 in an improved and substantially leak-free manner to prevent undesired leakage of modification about the exterior of the cannula, and corresponding undesired nondelivery of medication to the patient.

As shown in FIGS. 1 and the illustrative subcutaneous injection set 10 is constructed generally in accordance with the injection set described and claimed in U.S. Pat. No. 4,755,173, which is incorporated by reference herein. More particularly, the injection set 10 includes the housing 14 which is preferably constructed from a lightweight molded plastic or the like to include an internal chamber 16 and a fitting 18 adapted for connection to a delivery tube 20.

The medication or other selected fluid is supplied from the components (not shown) of, a external infusion system through the delivery tube 20 to the internal chamber 16. In this regard, FIG. 1 depicts a free end of the delivery tube 20 to include a standard luer connection 22 for connection to other infusion system components.

In the preferred geometry, the soft cannula 12 is constructed from polytetrafluorethylene (Teflon) or a polytetrafluorethylene-based material and is generally supported within an outlet bore 23 defined by a cylindrical support hub 24 of the housing 14 to protrude outwardly therefrom. The top end of the internal chamber 16 defines an opening 26 which is substantially closed by a resilient, self-sealing septum 28. This septum 28 is retained in position by an overlying cap 30 fixed onto the housing 14 by snap-fit or press-fit mounting, or by other, suitable attachment means.

Figure 2:
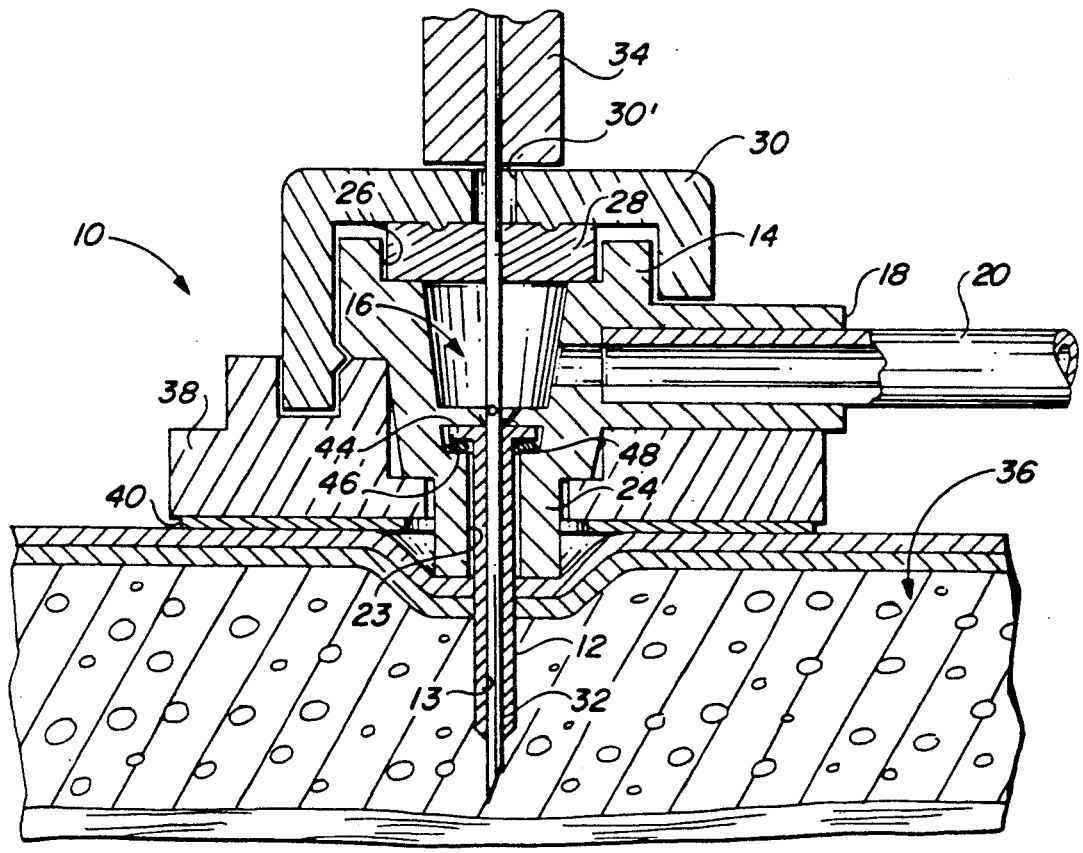
FIG. 2 is an enlarged fragmented sectional view illustrating the injection set for subcutaneous delivery of a selected medication or other infusion fluid to a patient.

An insertion needle 32 is initially mounted to extend from a manually accessible handle 34 through an aperture 30' in the cap, and further through the septum 28 into the internal chamber 16. As shown in FIG. 2, the insertion needle protrudes further through a lumen 13 defined by the cannula 12 to terminate in a sharp or pointed distal end disposed at least slightly beyond a corresponding distal end of the cannula.

In use, as described in U.S. Pat. No. 4,755,173, the cannula 12 is placed transcutaneously at a selected fluid injection site on the skin 36 (FIG. 2) of a patient. Such placement is achieved by piercing the skin with the insertion needle 32 to simultaneously position the needle 32 and cannula 12 transcutaneously. A holding pad 38 is desirably positioned at an underside of the housing 14 and has a convenient size and shape for easy manipulation to facilitate cannula placement.

An adhesive film 40 (FIG. 2) on the holding pad 38 is exposed upon removal of a peel-off strip 42 and functions to releasably retain the entire injection set 10 at a desired site on the patient's skin. When proper transcutaneous cannula placement is obtained, the insertion needle 32 is normally removed by withdrawal through the septum 28, thus leaving the cannula 12 in place with the lumen 13 therein defining an open path for subcutaneous fluid injection into the patient.

In accordance with the improved cannula mounting arrangement of the present invention, the cannula 12 is captured within the cylindrical support hub 24 in a sealed manner to confine infusion fluid flow to the cannular lumen 13. In other words the infusion fluid which is normally supplied to the housing 14 under positive pressure is prevented from leaking between the hub 24 and the exterior of the cannula.

Figure 3:
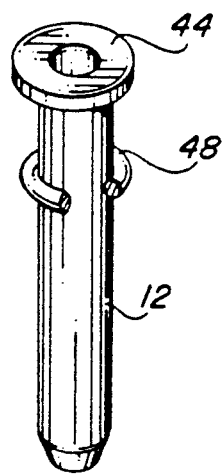
FIG. 3 is a fragmented perspective view illustrating a soft cannula and associated sealing gasket for use in the injection set of FIGS. 1 and 2.

More specifically, as shown in FIGS. 2 and 3, the cannula 12 has a base end defining a radially outwardly extending flange 44. This flange 44 is sized to prevent cannula removal from the housing in an outward direction through the support hub 24. Moreover, the flange 44 is sized to fit into a shallow cylindrical well 46 formed within the internal chamber 16 at a position immediately upstream from the support hub 24.

An annular sealing gasket 48 is fitted about the cannula 12 and is axially compressed between the cannular flange 44 and an annular seat 50 surrounding the upstream end of the support hub at a base of the well 46. The sealing gasket 48 of the preferred embodiment is an elastomeric O-ring made of silicone rubber, with a hardness of approximately 60 on the Shore A scale. Alternately, the sealing gasket 48 may comprise a segment of cylindrical follow tubing. Lock rim 52 is formed as part of the housing 14 to protrude radially inwardly in overlying relation to the flange 44 to maintain the sealing gasket 48 under compression. With this construction, the gasket 48 provides a highly effective seal preventing fluid leakage to the exterior of the cannula.

The cannula 12 and the associated sealing gasket 48 are quickly and easily installed into the housing 14 by use of a suitable swage tool 54, prior to assembly of the housing 14 with the septum 28 and associated cap 30. In particular, as viewed in FIGS. 4 and 5, the cannula 12 and the sealing gasket 48 are installed within the housing to position the flange 44 within the well 46. In this position, the sealing gasket 48 is interposed axially between the flange 44 and the adjacent annular seat 50.

Figure 4:
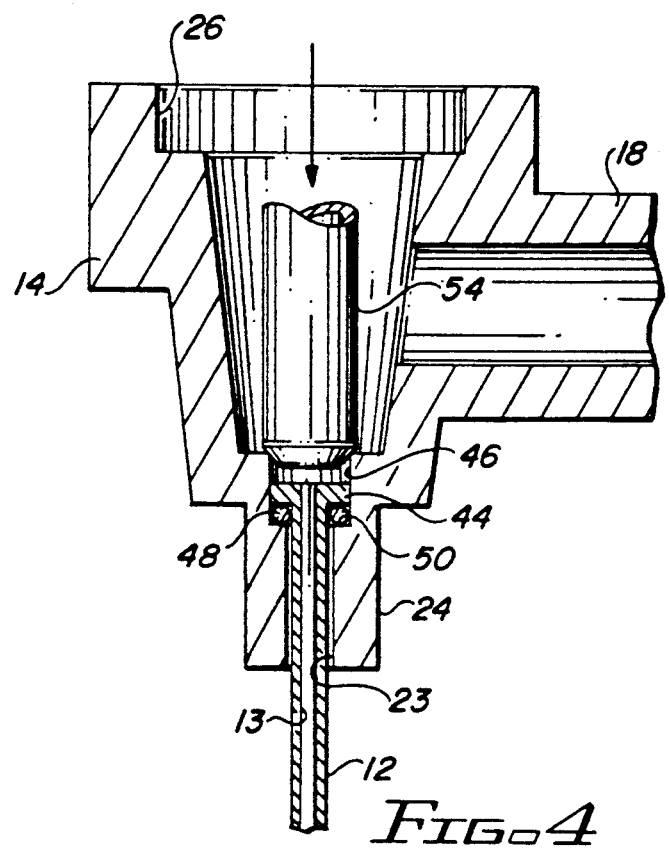
FIG. 4 is a fragmented sectional view illustrating insertion of a swage tool into an injection set housing for mounting the cannula thereto.
Figure 5:
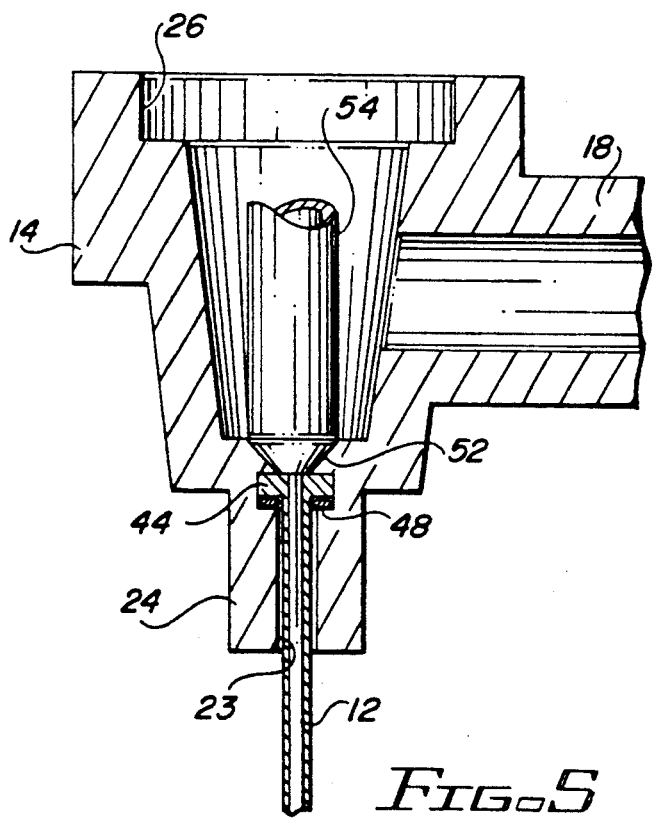
FIG. 5 is a fragmented vertical section similar to FIG. 4, but illustrating further advancement of the swage tool to mount the cannula.

The swage tool 54, preferably in the form of a sonic horn having a beveled leading edge is then advanced into the internal chamber 16 through the opening 26 to engage an annular corner defining the upper edge of the well 46 (FIG. 4). Further advancement of the tool 54 and appropriate energization thereof causes the engaged plastic housing material to deform and flow downwardly and radially inwardly according to the shape of the beveled tool edge (FIG. 5). This step effectively re-shapes a small amount of the plastic housing material to form the lock rim 52 in overlying engagement with the flange 44. Importantly, the tool 54 is advanced sufficiently such that the lock rim 54 positions the cannular flange 44 to maintain the sealing gasket 48 under at least slight compression. The tool 54 is then withdrawn, and further assembly of the injection set 10 may proceed.

The subcutaneous injection set of the present invention thus provides an improved mounting apparatus and method for substantially leak-free cannula function.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention. Accordingly, no limitation on the invention is intended by way of the foregoing description and accompanying drawings, except as set forth in the appended claims.

What is claimed is:

1. A subcutaneous injection set, comprising:

a one piece housing defining an internal chamber adapted to receive a selected infusion fluid, and further defining a generally cylindrical support hub having an outlet bore formed therein and a generally annular seat surrounding said outlet bore at an upstream end thereof within said chamber;

a cannula having a base end defining a radially outwardly extending flange, said cannula being received within said outlet bore with said flange generally overlying said annular seat, said cannula protruding outwardly from said housing;

sealing means interposed between said flange and said annular seat; and a radially inwardly extending annular lock rim swaged in the interior of said housing and overlying at least a portion of said flange to retain said flange in a position relative to said seat to compress said sealing means.

2. The subcutaneous injection set of claim 1, wherein said sealing means comprises:

an annular sealing gasket of a resilient material.

3. The subcutaneous injection set of claim 2, wherein said annular sealing gasket comprises:

an O-ring made of elastomeric material.

4. The subcutaneous injection set of claim 3, wherein said elastomeric material is silicone rubber.

5. The subcutaneous injection set of claim 4, wherein said silicone rubber has a hardness of approximately 60 on the Shore A scale.

6. The subcutaneous injection set of claim 2, wherein said annular sealing gasket comprises:

a segment of hollow cylindrical tubing.

7. The subcutaneous injection set of claim 1, wherein said cannula is a soft cannula.

8. The subcutaneous injection set of claim 7, wherein said cannula is made of polytetrafluorethylene.

9. A subcutaneous injection set, comprising:

a one piece housing defining an internal chamber adapted to receive a selected infusion fluid, and further defining a generally cylindrical support hub having an outlet bore formed therein and a generally annular seat surrounding said outlet bore at an upstream end thereof within said chamber;

a cannula having a base end defining a radially outwardly extending flange, said cannula being received within said outlet bore with said flange generally overlying said annular seat, said cannula protruding outwardly from said housing;

an annular sealing gasket interposed between said flange and said annular seat; and a lock rim swaged within said housing chamber in engagement with said flange to maintain said flange in a position with said sealing gasket retained compressively between said flange and said seat.

10. A method of mounting a cannula to a housing in a subcutaneous injection set, wherein the housing defines an internal chamber adapted to receive a selected infusion fluid and a cylindrical support hub having an outlet bore formed therein, and further wherein the cannula has a base end defining an outwardly extending flange, said mounting method comprising the steps of:

forming a generally annular seat in the housing in surrounding relation to an upstream end of the outlet bore within the housing chamber;

mounting a sealing gasket about the cannula;

installing the cannula within the outlet bore, with the sealing gasket interposed between the flange and the seat; and swaging a portion of the housing to form a lock rim in engagement with the flange, said swaging step securing the flange in a position within the housing chamber such that the sealing is compressively retired between the flange and the seat.

11. The method of claim 10, wherein said swaging step comprises:

a sonic swaging step.

12. The method of claim 10, wherein said forming step includes forming a shallow well within the housing chamber at the upstream end of the outlet bore, with a base portion of the well defining the seat, said cannula installing step including placing the flange within the well, and said securing step including swaging a portion of the housing defining the well to form the lock rim overlying and engaging the flange.

* * * * *